United States Patent [19]

Brickhouse

[11] Patent Number: 4,905,510
[45] Date of Patent: Mar. 6, 1990

[54] METHOD OF ISOLATING AN OILFIELD FLOWLINE SAMPLE FOR ANALYSIS WITHOUT SHEARING THE SAMPLE

[75] Inventor: Paul E. Brickhouse, Houston, Tex.

[73] Assignee: Texaco Inc., White Plains, N.Y.

[21] Appl. No.: 287,309

[22] Filed: Dec. 21, 1988

[51] Int. Cl.$^4$ ............................................. F21B 49/00
[52] U.S. Cl. ..................................... 73/155; 73/863.84
[58] Field of Search ................ 73/155, 863.83, 863.84, 73/863.86

[56] References Cited

U.S. PATENT DOCUMENTS

| | | | |
|---|---|---|---|
| 4,346,609 | 8/1982 | Diesel | 73/863.84 |
| 4,470,316 | 9/1984 | Jiskoot | 73/863.84 |
| 4,527,436 | 7/1985 | Jones | 73/863.84 |

*Primary Examiner*—John Chapman
*Assistant Examiner*—Kevin O'Shea
*Attorney, Agent, or Firm*—Jack H. Park; Kenneth R. Priem; Harold J. Delhommer

[57] ABSTRACT

The invention is a method for isolating a sample of oilfield production without shearing the sample, which includes a multistep method of using a chamber to isolate a sample of fluid from a flowline by transferring the sample from the flowline without a significant pressure drop. This involves placing a valved isolation chamber in fluid communication with a sampling port of an oilfield production flowline, the isolation chamber consists of a closed vessel, a first entry port into the vessel, and a first exit port out of the vessel controlled by a first valve. The sampling port valve is opened while the first valve of the isolation chamber is closed to permit pressure within the isolation chamber to equalize with pressure within the flowline. The first valve is then opened to permit oilfield production to pass from the flowline through the sampling port and the first entry port into the isolation chamber and out of the first valve. The first valve is closed, then the sampling port valve is closed to trap a sample within the isolation chamber.

19 Claims, 1 Drawing Sheet

METHOD OF ISOLATING AN OILFIELD FLOWLINE SAMPLE FOR ANALYSIS WITHOUT SHEARING THE SAMPLE

BACKGROUND OF THE INVENTION

This invention relates to a method for examining samples of oilfield flowlines. More particularly, the invention method concerns the isolation of a flowline sample without shearing the sample so that a more accurate examination of the flowline sample can be performed.

In the oilfield, production flowlines carry produced fluids from production wells to processing facilities. Because of the nature of oil production, particularly in older fields, and more particularly where fluids have been injected into the reservoir to enhance oil production, the produced fluids contain a large volume of water in proportion to produced oil.

Produced water is more than an inconvenience. The water must be separated from the produced oil. This is generally done with a combination of mechanical oil and water separators and chemical treating. Water treating chemicals are normally injected in the field upstream of mechanical oil and water separators to take full advantage of the natural agitation that occurs in petroleum flowlines. Thus, most of the oil droplet coalescence occurs in flowlines upstream of separators. Flowlines are also commingled from various wells into a common oil and water separator. As a rule, only the overall separation performance of the oil and water separator can be monitored.

Attempts to monitor the water quality of individual flowlines to check on the chemical treatment needed for each individual flowline have failed. If samples are removed from individual flowlines, the coalesced oil droplets shear as they pass through a pressure drop. A measurable pressure drop across a valve of one psi or more can cause substantial shearing. Consequently, samples drawn from flowlines are inaccurate measures of the success of chemical treatment in the flowlines prior to the oil and water separators. In some cases, the sheared samples become reverse oil-in-water emulsions as bad as those existing at the production wellhead prior to chemical treatment in the flowline.

SUMMARY OF THE INVENTION

The invention is a method for isolating a sample of oilfield production for analysis without shearing the sample, which comprises a multistep method of using a chamber to isolate a sample of fluid from a flowline by transferring the sample from the flowline without a significant pressure drop. This involves placing an isolation chamber in fluid communication with a sampling port of an oilfield production flowline. The isolation chamber comprises a closed vessel, a first entry port into the vessel, and a first exit port out of the vessel controlled by a first valve. The sampling port of the flowline is also controlled by a valve.

The sampling port valve is opened while the first valve of the isolation chamber is closed to permit pressure within the isolation chamber to equalize with pressure within the flowline. The first valve is then opened to permit oilfield production to pass from the flowline through the sampling port and the first entry port into the isolation chamber and out of the first valve. The first valve is then closed. The sampling port valve is thereafter closed, isolating a sample within the isolation chamber. The oilfield production fluid sample contained within the isolation chamber is allowed to separate for a period of time before a sample of fluid from the isolation chamber is removed for examination.

DETAILED DESCRIPTION

Figure 1:
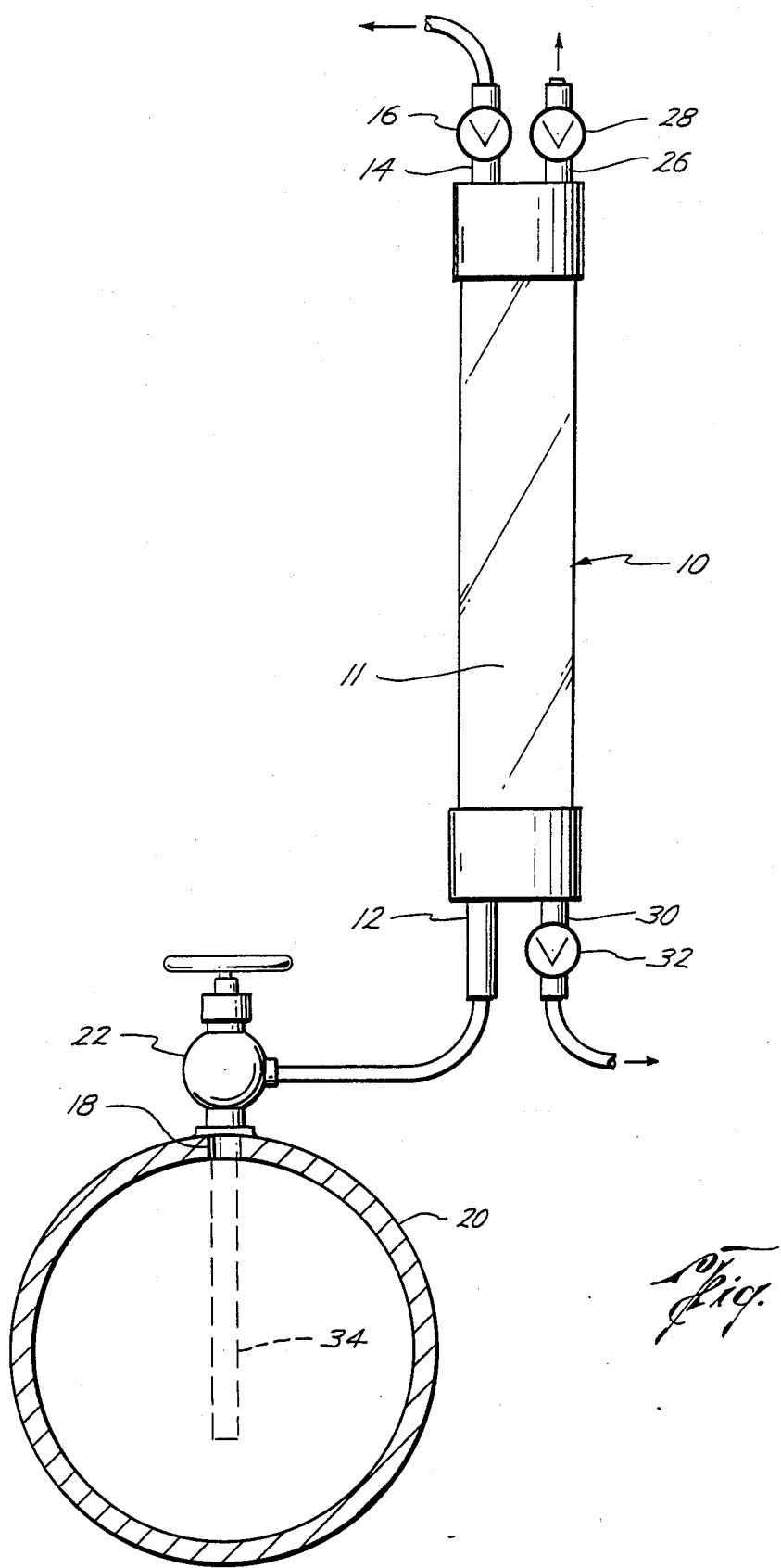
FIG. 1 is a plan view of a preferred isolation chamber attached to a flowline which may be used in the invention process.

The invention provides a method to enable an engineer to examine accurate samples from oilfield production flowlines. It allows for the determination of actual in-line water quality upstream of an oil and water separator. This is done by isolating a fluid sample without the water and oil fluid mixture crossing a high shear zone.

An accurate determination of water quality upstream of an oil and water separator allows for the effectiveness of chemical treating in the flowline to be determined. The chemical treating in each individual flowline can be optimized independently of other flowlines. Consequently, substantial money can be saved in chemical treating costs by not overtreating production flowlines with excess chemicals. This method may also be used to project the treating capacity of a downstream separator for design planning and for troubleshooting equipment already placed in service. The invention has particular value in fields with a high water production, such as mature fields, or fields under waterflood or steam flood.

The invention allows for a sample to be removed from production flowlines without exposing the fluid sample to shear as it crosses the sampling port valving. An isolation chamber 10 which comprises a closed vessel 11, a first entry port 12 into the vessel, and a first exit port 14 out of the vessel controlled by a first valve 16, is placed in fluid communication with a sampling port 18 of an oilfield production flowline 20, said sampling port being controlled by a valve 22. The sampling port valve 22 is opened while the first valve 16 is closed to permit pressure within the isolation chamber to equalize with pressure within the first entry port 12 and the flowline 20. The first valve 16 is opened to permit oilfield production to pass from the flowline 20 through the sampling port valve 22 and the first entry port 12 into the isolation chamber 10 and out of the first valve 16. By this means, most of the fluid which initially passes into the isolation chamber 10 with a pressure drop over the sampling port 18 and valve 22 is exhausted out of the isolation chamber 10 through the first valve 16, and the production fluid remaining in the isolation chamber 10 has been subjected to very low shear entering the isolation chamber 10 from the flowline 20.

The first valve 16 is then closed, followed by the closing of the sampling port valve 22. The oilfield production fluid contained within the isolation chamber 10 is then allowed to separate for a period of time, preferably from about 15 seconds to about 2 hours, more preferably from about 3 minutes to about 30 minutes. Finally, a sample of the trapped fluid is removed from the isolation chamber for visual and analytical examination.

To allow for ease of operation in the field, the first valve may be opened to equalize chamber pressure with atmospheric pressure after allowing the fluid to separate within the chamber for a period of time and before removing a fluid sample for examination. This allows a sample to be removed and examined at atmospheric pressure. With some lighter gravity crudes, some gas may flash off, giving the oil increased buoyancy and artificial lift. This can be controlled by a slow process of equalizing pressure with atmospheric pressure, particularly if flowline pressure is high relative to atmospheric pressure.

The invention method of trapping a fluid sample from a production flowline without shearing the sample is easier to accomplish if the isolation chamber contains additional valves, eliminating the need for one valve to be used for multiple purposes. It is preferred for the isolation chamber 10 to have a second exit port 26 controlled by a second valve 28, and a third exit port 30 controlled by a third valve 32. The second exit port 26 and second valve 28 may be opened to equalize chamber pressure with atmospheric pressure after allowing the fluids to separate within the chamber for a period of time and before removing a fluid sample for examination. By the use of the second exit port 26 and valve 28, the first exit port 14 may remain in fluid communication with a waste dump. The third exit port 30 controlled by a third valve 32 may be used to remove a sample of fluid for examination.

Preferably, the port from which a sample is taken is briefly flushed with sample that is discarded prior to taking a sample for analysis. For a clean sample of water containing 5-10 ppm of oil, a preliminary flush is not crucial, but will improve the accuracy of the sample. If the water contains as much as 1% oil, a separate exit port and valve used only for withdrawing a sample from the isolation chamber is desired.

Ideally, the vessel is transparent. Transparent walls permit visual observation of the physical condition of the fluid sample contained within. This allows for more accurate determination of the needed separation time before a fluid sample is withdrawn for examination. To achieve transparent walls, the vessel may be constructed of transparent acrylic, polycarbonate, or other strong transparent materials.

In an effort to further reduce any pressure difference between the isolation chamber and the production flowline, the isolation chamber may be charged with an inert gas such as nitrogen or helium to the pressure of the flowline prior to opening the sampling port valve while the first valve is closed.

Some production flowlines may have stratified flow, wherein the production has split into a top oil phase and bottom water phase. This generally occurs when the water to oil ratio is relatively low and there is sufficient oil to form a separate phase. In such a case, the sampling port should be one which will withdraw a flowline fluid from the middle to the bottom of the flowline to provide a more representative water sample from the flowline. Another option is to insert a stinger probe 34, basically a piece of tubing, through the sampling port 18 to withdraw flowline fluid from the middle to the bottom of the flowline 20. In addition, it is preferred for the sampling port valve 22 to be a full open ball valve in order to minimize any pressure drop and subsequent shear which may occur as fluid leaves the flowline 20 to travel into the isolation chamber 10.

This method of isolating fluid samples from production flowlines upstream of an oil and water separator has been successfully used to optimize chemical treating at the Kern River Field in California. With this method, flowline water quality was examined visually. Where the water looked clear, the chemical addition rate was decreased upstream in order to minimize cost. Where the water seemed oily, the chemical rate was adjusted to provide better water quality. In some cases, more effective chemical injection points were located and put into service to provide superior water quality at lower chemical cost. Overall chemical injection rates were reduced at the same time effluent water quality was improved.

The invention method was critical to the program of optimizing chemical treating of production fluids since samples from nearly every flowline had previously been thought to be bad to very bad reverse oil-in-water emulsions. This false information from the previous method of collecting samples had lead to the belief that many of the flowlines were being undertreated chemically when in fact chemical treatment was acceptable or too high.

Many other variations and modifications may be made in the concepts described above by those skilled in the art without departing from the concepts of the present invention. Accordingly, it should be clearly understood that the concepts disclosed in the description are illustrative only and are not intended as limitations on the scope of the invention.

What is claimed is:

1. A method for isolating an oilfield production flowline sample for analysis without shearing the sample, which comprises:
    placing an isolation chamber in fluid communication with a sampling port of an oilfield production flowline,
    said isolation chamber comprising a closed vessel, a first entry port into the vessel, and a first exit port out of the vessel controlled by a first valve,
    said sampling port controlled by a valve;
    opening a sampling port valve while the first valve is closed to permit pressure within the isolation chamber to equalize with pressure within the first entry port and the flowline;
    opening the first valve to permit oilfield production to pass from the flowline through the sampling port and the first entry port into the isolation chamber and out of the first valve;
    closing the first valve;
    closing the sampling port valve;
    allowing the oilfield production fluid contained within the isolation chamber to separate for a period of time, and
    removing a sample of fluid from the isolation chamber for examination.

2. The method of claim 1, further comprising opening the first valve to equalize chamber pressure with atmospheric pressure after allowing the fluid to separate within the chamber for a period of time and before removing a fluid sample for examination.

3. The method of claim 1, wherein the first exit port and first valve are located at the opposite end of the isolation chamber from the first entry port.

4. The method of claim 1, wherein the isolation chamber further comprises a second exit port controlled by a second valve.

5. The method of claim 4, further comprising opening the second valve to equalize chamber pressure with atmospheric pressure after allowing the fluid to separate within the chamber for a period of time and before removing a fluid sample for examination.

6. The method of claim 5, wherein the isolation chamber further comprises a third exit port controlled by a third valve.

7. The method of claim 6, further comprising opening the third valve to remove the sample of fluid for examination.

8. The method of claim 1, wherein the sampling port valve is a full open ball valve.

9. The method of claim 1, wherein the sampling port withdraws flowline fluid from the middle of the flowline to provide a representative fluid sample of the flowline.

10. The method of claim 1, further comprising inserting a stinger probe through the sampling port to withdraw flowline fluid from the middle of the flowline.

11. The method of claim 1, wherein the vessel is transparent.

12. The method of claim 11, wherein the vessel is made of acrylic.

13. The method of claim 11, wherein the vessel is made of polycarbonate.

14. The method of claim 1, wherein the fluid contained within the isolation chamber is allowed to separate for about 15 seconds to about 2 hours.

15. The method of claim 1, wherein the oilfield production comes from a steamflood.

16. The method of claim 1, wherein the oilfield production comes from a waterflood.

17. The method of claim 1, further comprising charging the isolation chamber with an inert gas to the pressure of the flowline prior to opening the sampling port valve while the first valve is closed.

18. A method for isolating an oilfield production flowline sample for analysis without shearing the sample, which comprises:

placing an isolation chamber in fluid communication with a sampling port of an oilfield production flowline upstream of an oil and water separator, said isolation chamber comprising a closed transparent vessel, a first entry port into the vessel, a first exit port out of the vessel controlled by a first value, a second exit port out of the vessel controlled by a second valve, and a third exit port out of the vessel controlled by a third valve, said first exit port and first valve located at the opposite end of the isolation chamber from the first entry port, said sampling port controlled by a full open ball valve;

charging the isolation chamber with an inert gas to the pressure of the production flowline;

opening a sampling port valve while the first valve, second valve and third valve are closed;

opening the first valve to permit oilfield production to pass from the flowline through the sampling port and the first entry port into the isolation chamber and out of the first valve;

closing the first valve;

closing the sampling port valve;

allowing the oilfield production fluid contained within the isolation chamber to separate for about 15 seconds to about 2 hours;

opening the second valve to equalize chamber pressure with atmospheric pressure; and opening the third valve to remove a sample of fluid from the isolation chamber for examination.

19. The method of claim 18, further comprising flushing the third exit port with a small volume of chamber contained sample before removing the sample of fluid for examination.

* * * * *